United States Patent [19]

Hori et al.

[11] Patent Number: 4,804,935

[45] Date of Patent: Feb. 14, 1989

[54] SENSOR FOR MEASUREMENT BY ELECTRICAL HEATING AND METHOD FOR MANUFACTURE OF THE SAME

[75] Inventors: Tomoshige Hori, Kitamoto; Kensuke Itoh, Kodaira, both of Japan

[73] Assignee: Snow Brand Milk Products Co., Ltd., Japan

[21] Appl. No.: 5,663

[22] Filed: Jan. 21, 1987

[30] Foreign Application Priority Data

Feb. 27, 1986 [JP] Japan ................................ 61-42540

[51] Int. Cl.[4] ............................................. H01C 3/04
[52] U.S. Cl. ..................................... 338/25; 338/267; 338/268; 338/269; 338/270; 29/610.1; 29/612; 374/185
[58] Field of Search ................. 338/25, 22 R, 28, 292, 338/294, 267, 268, 269, 270; 29/592 R, 610.1, 611, 612, 613; 374/165, 179, 183, 185

[56] References Cited

U.S. PATENT DOCUMENTS

| | | | |
|---|---|---|---|
| 3,845,443 | 10/1974 | Fisher | 338/292 X |
| 3,939,557 | 2/1976 | Rendle | 29/610.1 X |
| 4,222,025 | 9/1980 | Iles et al. | 338/28 X |
| 4,462,020 | 7/1984 | May | 29/612 X |
| 4,523,177 | 6/1985 | Driggers | 338/270 X |
| 4,603,026 | 7/1986 | Martin | 374/185 X |

*Primary Examiner*—E. A. Goldberg
*Assistant Examiner*—M. M. Lateef
*Attorney, Agent, or Firm*—Griffin, Branigan & Butler

[57] ABSTRACT

A sensor for electrical heating measurement has a core rod which is partly reduced in diameter to form an annular recess, an inner electrically insulating layer formed within the annular recess, a thin metal wire wound about the inner electrically insulating layer, an outer electrically insulating layer covering the metal wire winding and being flush with the outer circumferential surface of the core rod, and a metal sleeve being in intimate contact with the outer circumferential surface of the core rod throughout the overall length thereof.

4 Claims, 6 Drawing Sheets

SENSOR FOR MEASUREMENT BY ELECTRICAL HEATING AND METHOD FOR MANUFACTURE OF THE SAME

BACKGROUND OF THE INVENTION

This invention generally relates to a sensor used for so-called electrical heating measurement in which a metal member is inserted in various liquid materials or semi-solid materials, the metal member is heated under the application of electrical current up to a higher temperature than that of the surrounding material, and changes in parameter of the metal member are continuously measured in relation to time lapse to detect changes in state of the material, and more particularly, it relates to this type of sensor which is workable for bending with high reliability and a manufacture method therefor.

The inventors of this application have already proposed, in Japanese Patent Application No. 60-197230, a sensor for electrical heating measurement comprising a core rod covered with an electrically insulating member, a thin metal wire wound about the core, and an electrically insulating member covering the thin metal wire.

Since in the proposed sensor the thin metal wire is wound about the core rod so that the length of the wire can be increased as compared to the usual straight wire to increase electrical resistance of the wire, the amount of generated heat per unit length of the sensor is increased proportionally, thereby making it possible to reduce the amount of current for obtaining required sensitivity. Further, for the sake of obtaining the same amount of heat generation, the length of the sensor can be decreased as compared to a sensor using the straight wire.

In addition, the thin metal wire wound about the core rod is improved in its shock proof properties and is not therefore liable to break. Also, the thin metal wire covered, interiorly and exteriorly thereof, with the electrically insulating members will not erode, for example, a tank for storing milk under the influence of electrolytic corrosion.

Accordingly, the curdy state of milk can be examined in a milk curdling process by inserting the sensor in the milk and by measuring temperatures of the thin metal wire in relation to time lapse while passing an electrical current intermittently or continuously through the thin metal wire.

The sensor constructed as above has many advantages but is still disadvantageous in that it does not have enough mechanical strength to be workable for stable bending. This is because during bending, pin holes are developed in the outer cover and its mechanical strength is degraded locally.

SUMMARY OF THE INVENTION

An objective of this invention is to eliminate the aforementioned disadvantages of the prior art sensor and to provide a sensor for electrical heating measurement which is workable for bending with high reliability.

According to this invention, the above objective can be accomplished by a sensor for electrical heating measurement comprising a core rod which is partly reduced in diameter to form an annular recess, an inner electrically insulating layer formed within the annular recess, a thin metal wire wound about the inner electrically insulating layer, an outer electrically insulating layer covering the thin metal wire winding and being flush with the outer circumferential surface of the core rod, and a metal sleeve being in intimate contact with the outer circumferential surface of the core rod throughout the overall length thereof.

With the above technical means, the same effects as those attained by the prior art sensor can of course be fulfilled and in addition, the metal sleeve is united to the core rod to form a unitary rod as a whole because the metal sleeve is in intimate contact with the outer electrically insulating layer and the outer circumferential surface of the core rod and therefore, if portions excepting a heat generator located within the recess are worked to bend, the heat generator will not be damaged.

The sensor of the above construction can preferably be connected to closely spaced mount positions by bending the sensor at axially outer portions contiguous to the opposite ends of the recess, thereby simplifying mounting of the sensor to, for example, a fluid tank. If, as in the prior art sensor, bending is accompanied by mechanical damage, opposite end portions of the sensor must be connected directly to diametrally opposing positions or indirectly to closely spaced mount positions through the medium of special bent members. Disadvantageously, this requires a wide space reserved for mounting of the sensor or leads to a complicated sensor mount structure.

Preferably, the thin metal wire winding is formed into a non-inductive winding by folding a single metal wire into two wire lines and winding the two wire lines toroidally such that the two lines do not come into contact with each other. The non-inductive winding is effective to protect the sensor against the influence of external electromagnetic disturbance.

The sensor of this invention described hereinbefore can be manufactured by uniformly reducing the diameter of a portion of a core rod made of a workable material over a length, applying electrical insulation to the reduced diameter portion, winding a thin metal wire about the electrical insulation, filling an electrically insulating material in the entire reduced diameter portion such that the thin metal wire is completely embedded in the electrically insulating material to thereby make uniform the outer diameter throughout the overall length of the core rod, fitting on the core rod a metal pipe having an inner diameter slightly larger than the outer diameter of the core rod, and cold drawing a resulting structure to bring the metal pipe into intimate contact with the electrically insulating material.

DESCRIPTION OF THE PREFERRED EMBODIMENT

The invention will now be described by way of example with reference to the accompanying drawings.

Figure 1A:
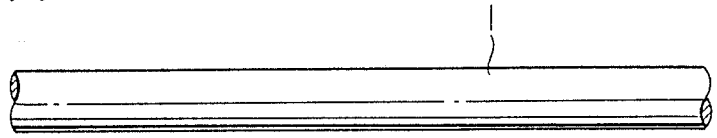
FIGS. 1A to 1G illustrate sequential steps of manufacture of a sensor according to the invention.
Figure 1B:
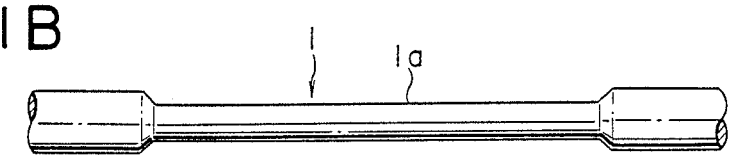
Figure 1C:
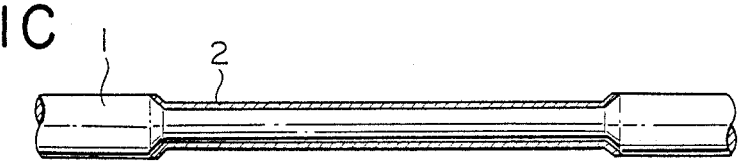
Figure 1D:
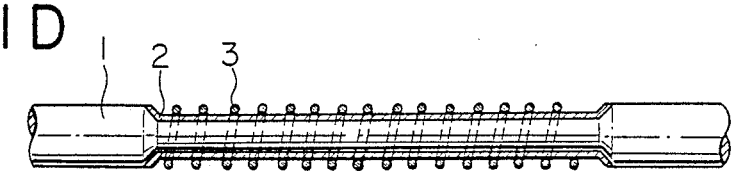
Figure 1E:
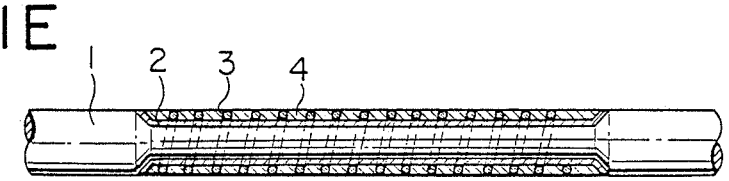
Figure 1F:
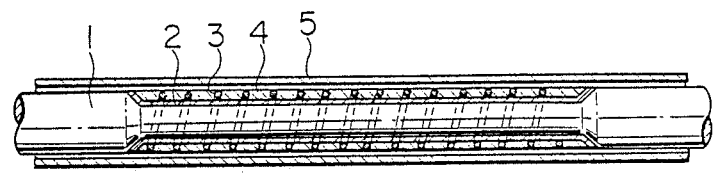
Figure 1G:
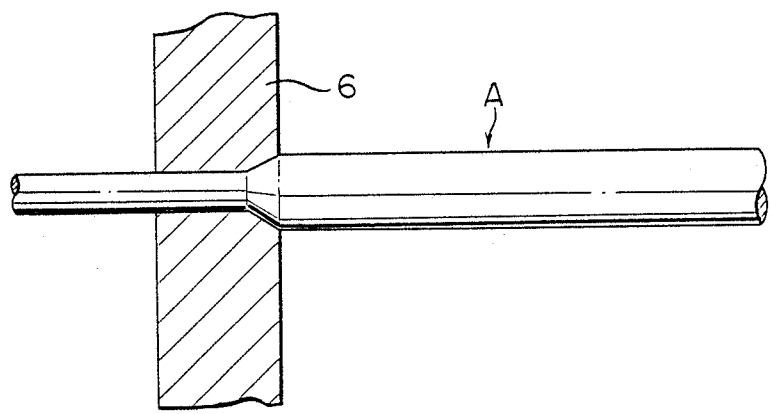

FIG. 1F illustrates a sensor for electrical heating measurement according to a preferred embodiment of the invention. A core rod 1 is made of a workable material such as teflon (polytetrafluoroethylene) or metal and has a portion which is reduced in diameter to form an annular recess 1a. An inner electrically insulating layer 2 is formed within the recess 1a and a thin metal wire 3 is wound about the inner electrically insulating layer 2. An outer electrically insulating layer 4 covers the thin metal wire winding so as to be flush with the outer circumferential surface of the core rod 1. The overall length of the core rod 1 is inserted into a metal sleeve 5. Although a slight gap is seen from an illustration in FIG. 1F between the core rod 1 and metal sleeve 5, the resulting structure of the two members is passed through a manufacture step as indicated in FIG. 1G so that the metal sleeve 5 may be brought into intimate contact with the outer circumferential surface of the core rod 1.

The sensor of the above construction can be manufactured as will be described below with reference to FIGS. 1A through 1G.

The diameter of a portion of a rod 1, made of teflon (polytetrafluoroethylene) or metal such as stainless, is first reduced uniformly over a length. The reduced diameter portion is denoted by reference numeral 1a.

Subsequently, electrical insulation is applied to the reduced diameter portion by covering the same with an electrically insulating material 2 such as teflon (polytetrafluoroethylene). A thin metal wire, for example, a platinum wire is wound about the electrical insulation 2 and an electrically insulating material 4 such as teflon (polytetrafluoroethylene) is then filled in the entire reduced diameter portion such that the platinum wire is completely embedded in the electrically insulating material 4 to thereby make uniform the outer diameter throughout the overall length of the core rod.

Thereafter, a metal pipe 5 of stainless having an inner diameter slightly larger than the outer diameter of the core rod 1 is fitted on the core rod and a resulting structure A is cold drawn to the end that the metal pipe 5 is brought into intimate contact with the outer circumferential surface of the core rod 1 and teflon (polytetrafluoroethylene) 4 (in FIG. 1G). A die 6 is used for cold drawing the structure A.

The cold drawing is meritorious because heat generated upon forced passage of the structure through the die 6 can be removed to prevent the metal components from changing in their properties to become fragile.

A single platinum wire 3 is not simply wound about the stainless rod 1. But, preferably, the winding is formed into a so-called non-inductive winding by folding a single platinum wire into two wire lines and winding the two wire lines toroidally such that they do not come into contact with each other.

Figure 2:
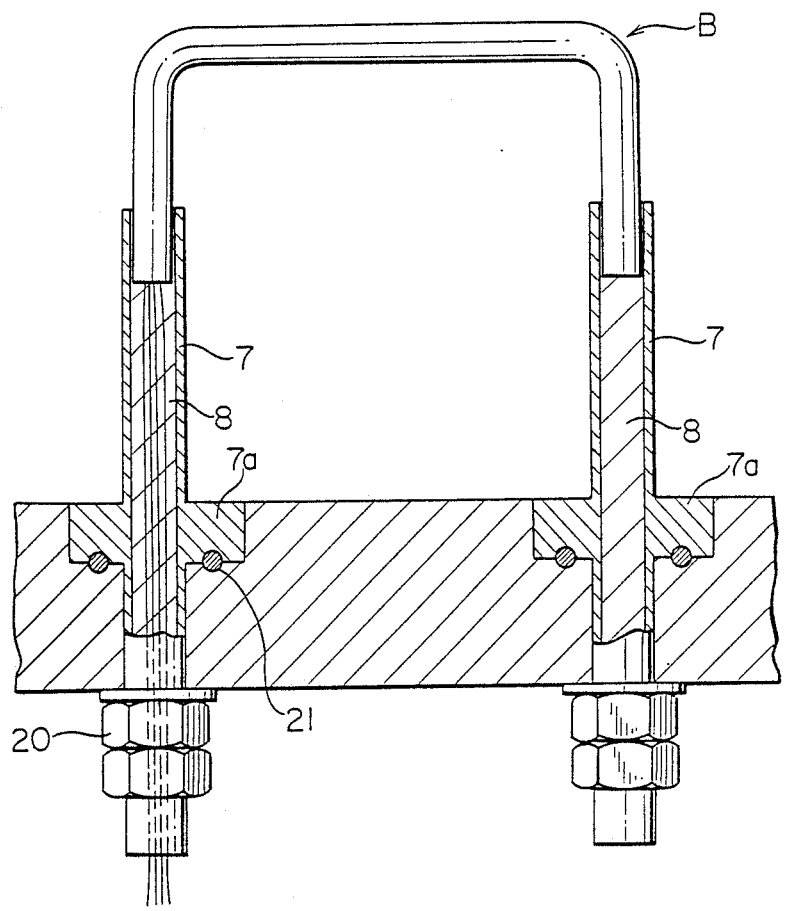
FIG. 2 is a fragmentary sectional view showing a state wherein opposite ends of the electrical heating sensor of the invention are connected to closely spaced amount positions.

An electrical heating sensor B prepared in accordance with the manufacture method described hereinbefore is exemplarily mounted as shown in FIG. 2. Leads are connected to respective ends of the platinum wire winding to permit four-terminal measurement. Through the four-terminal measurement, the influence of electrical resistances of the leads upon measurement results can be eliminated and so a desired length of leads, though amounting to, for example, 500 m or otherwise 1 km, may be used to obtain the same measurement result.

The sensor B is formed at its central portion with the annular recess 1a and the heat generator is located therein. Axially outer portions contiguous to the opposite ends of the heat generator are bent in the same direction to form a generally U-shaped measuring device. Each of the bent ends is welded to a metal pipe 7 and after the leads have been drawn out through the metal pipe 7, resin 8 is filled in the pipe 7. The metal pipe 7 has a flange 7a which is supported on a base provided on, for example, the wall of a fluid tank. By tightening nuts 20, the metal pipe 7 can be secured hermetically to the base through an O-ring 21.

As is clear from FIG. 2, by bending the opposite end portions of the sensor B in the same direction, the sensor can be connected at its opposite ends to close mount positions which are approximately spaced from each other by an axial length of the heat generator.

Figure 3:
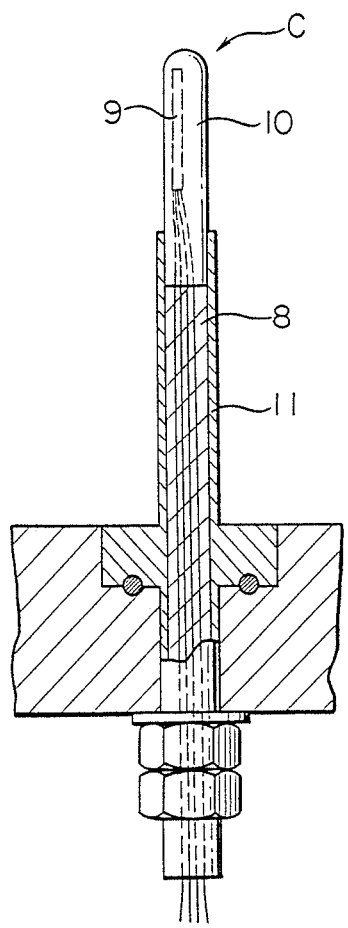
FIG. 3 is a fragmentary sectional view showing a state wherein a temperature measuring assembly is mounted.

The electrical heating sensor described previously is used in combination with a temperature measuring assembly C, as shown in FIG. 3, adapted to measure temperatures of fluid. The temperature measuring assembly has a temperature measuring resistor formed by winding a high resistance thin wire, for example, a platinum wire of 1 k$\Omega$. The temperature measuring resistor 9 is covered by a stainless pipe 10 which is welded to a stainless pipe 11. Four leads are drawn from the resistor 9 to ensure four-wire measurement and the stainless pipes 10 and 11 are filled with resin 8.

Figure 4:
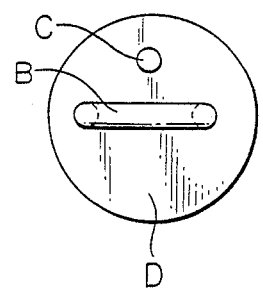
FIG. 4 is a diagram showing a mount layout of the sensor and temperature measuring assembly used in combination.

FIG. 4 shows a mount layout of the sensor B and temperature measuring assembly C used in combination. As shown, the sensor B is mounted to a base D in the diametral direction thereof and the temperature measuring assembly C is mounted at a site positioned on one of diametral lines which divide the base D into four parts.

Temperatures of fluid can be measured with high accuracy by means of the temperature measuring assembly C having the high resistance temperature measuring resistor. The electrical heating sensor is heated to a temperature which is substantially higher than a fluid temperature and the temperature difference therebetween is examined to decide a state of the fluid.

Figure 5:
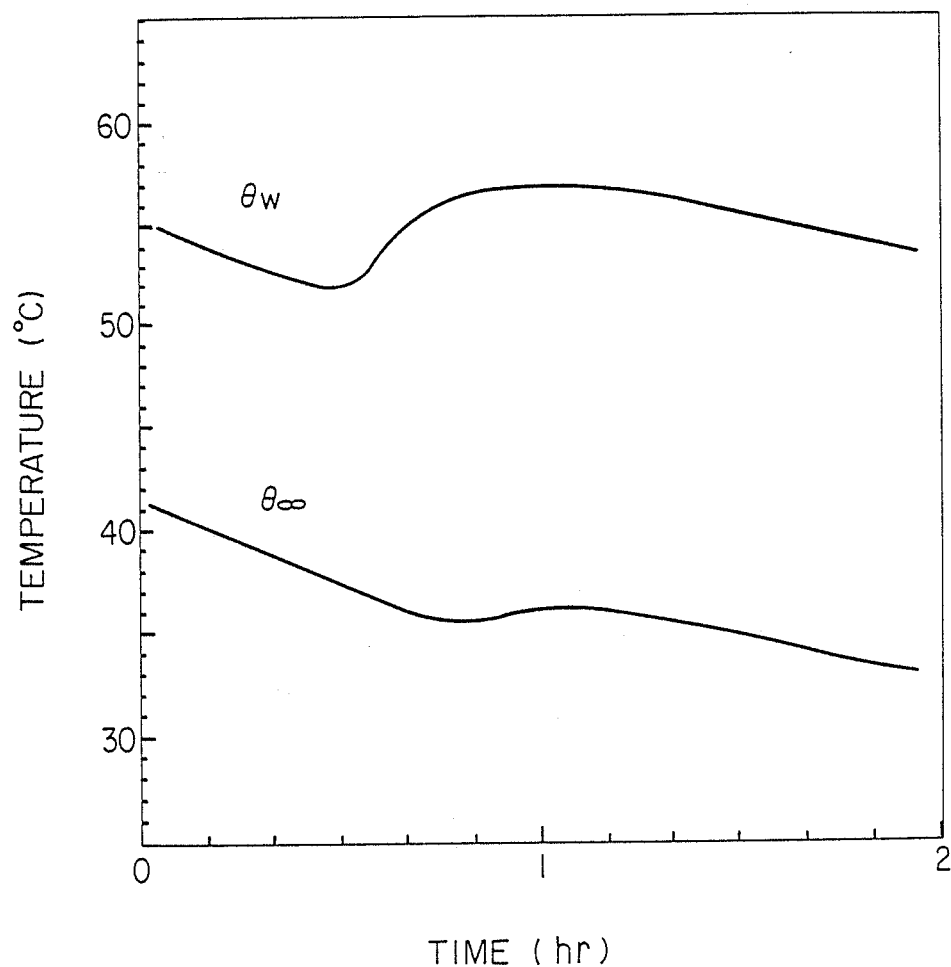
FIGS. 5 and 6 are graphs illustrating states of jelly measured using the electrical heating sensor and the temperature measuring assembly in combination.
Figure 6:
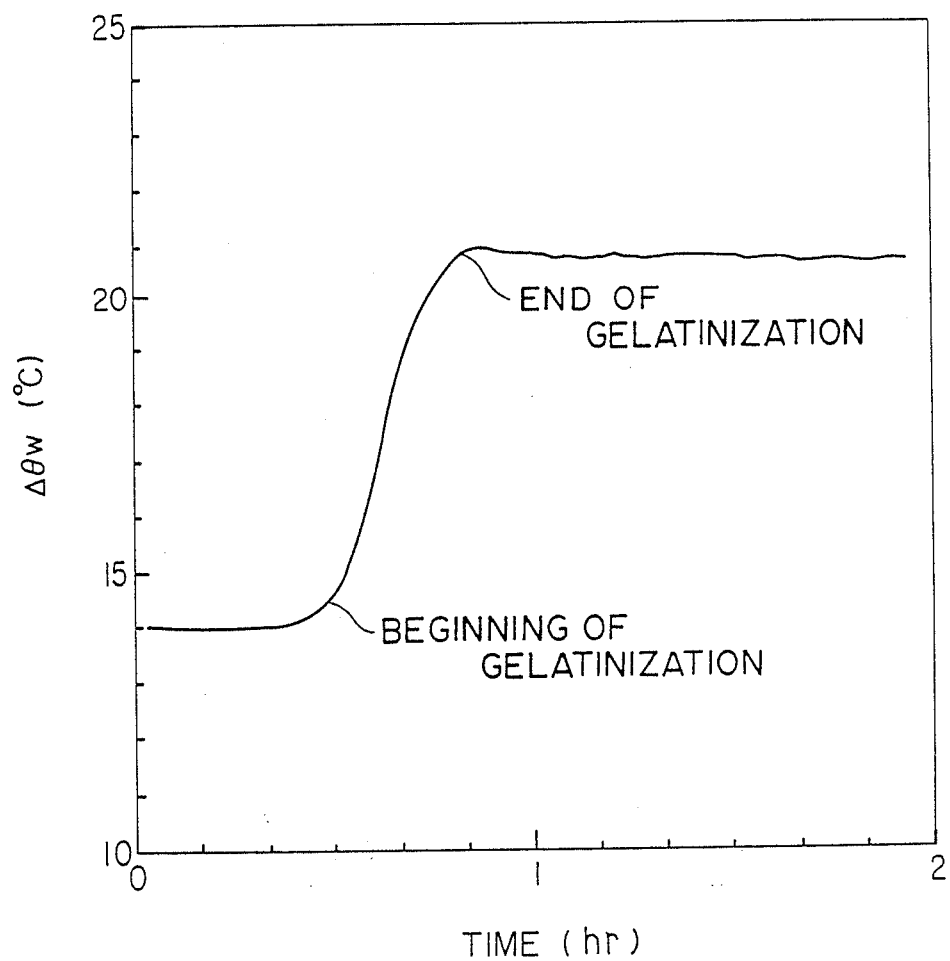

Exemplarily, the state of jelly is measured using in combination the sensor B and temperature measuring assembly C of FIG. 4 to obtain results as illustrated in FIG. 5 where $\theta w$ represents the temperature of the sensor and $\theta \infty$ the temperature of the fluid or jelly. By measuring changes in $\Delta \theta w = \theta w - \theta \infty$, the gelatinization start time and the gelatinization ending time can be detected as best indicated in FIG. 6. An offset gelatinization time indicates mal-blending. For cheese whose temperature remains unchanged throughout the preparation process, the measurement of the fluid temperature is not needed but in the case of jelly which is curdled while decreasing the temperature of fluid or jelly, the sensor of this invention is conveniently employed for the purpose of the simultaneous measurement of $\theta w$ and $\theta \infty$ and comparison therebetween.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. A sensor for electrical heating measurement comprising:
   a core rod which is partly reduced in diameter to form an annular recess;
   an inner electrically insulating layer formed within said annular recess;
   a thin metal wire wound about said inner electrically insulating layer;
   an outer electrically insulating layer covering the metal wire winding and being flush with the outer circumferential surface of said core rod; and
   a metal sleeve being in intimate contact with the outer circumferential surface of said core rod throughout the overall length thereof.

2. The sensor according to claim 1 wherein axially outer portions contiguous to the opposite ends of said annular recess are bent in the same direction.

3. The sensor according to claim 1 wherein said thin metal wire winding is a non-inductive winding formed by folding a single thin wire into two wire lines and winding the two wire lines toroidally such that they do not come into contact with each other.

4. A method for manufacture of an electrical heating sensor comprising the steps of:
   uniformly reducing the diameter of a portion of a core rod made of a workable material over a length;
   applying electrical insulation to be reduced diameter portion;
   winding a thin metal wire about said electrical insulation;
   filling an electrically insulating material in the entire reduced diameter portion such that said thin metal wire is completely embedded in said electrically insulating material to thereby make uniform the outer diameter throughout the overall length of said core rod;
   fitting on said core rod a metal pipe having an inner diameter slightly larger than the outer diameter of said core rod; and
   cold drawing a resulting structure to bring said metal pipe into intimate contact with said electrically insulating material.

* * * * *